United States Patent [19]

Nishimoto et al.

[11] Patent Number: 5,055,575
[45] Date of Patent: Oct. 8, 1991

[54] PROCESS FOR PREPARING 1,5-BENZOTHIAZEPINE DERIVATIVES

[75] Inventors: Shigeru Nishimoto, Minoo; Akio Nakao, Osaka; Yasuji Ikeda, Kyoto; Hiroyuki Nate, Higashiosaka, all of Japan

[73] Assignee: Tanabe Seiyaku Co., Ltd., Osaka, Japan

[21] Appl. No.: 516,940

[22] Filed: Apr. 30, 1990

Related U.S. Application Data

[63] Continuation-in-part of Ser. No. 507,929, Apr. 12, 1990, abandoned.

[51] Int. Cl.$^5$ .......................................... C07D 281/04
[52] U.S. Cl. .................................................... 540/491
[58] Field of Search ........................................ 540/491

[56] References Cited

U.S. PATENT DOCUMENTS 4,567,175  1/1986  Takeda et al. ...................... 540/491

FOREIGN PATENT DOCUMENTS 0098422  1/1984  European Pat. Off. ............ 540/491
2139620  11/1984  European Pat. Off. ............ 540/491
0343474  11/1989  European Pat. Off. ............ 540/491
0378455  7/1990  European Pat. Off. ............ 540/491

*Primary Examiner*—Robert T. Bond
*Attorney, Agent, or Firm*—Browdy and Neimark

[57] ABSTRACT

There is disclosed a process for preparing 1,5-benzothiazepine derivatives represented by the formula:

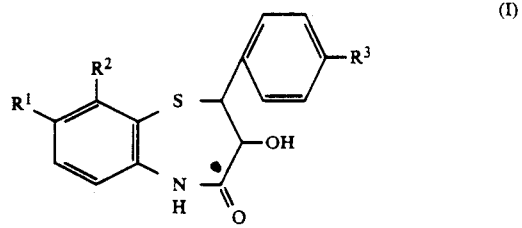

wherein one of $R^1$ and $R^2$ is a lower alkyl group or halogen atom, and the other is hydrogen atom, $R^3$ is a lower alkyl group or a lower alkoxy group, which comprises subjecting a propionic acid compound represented by the formula (II):

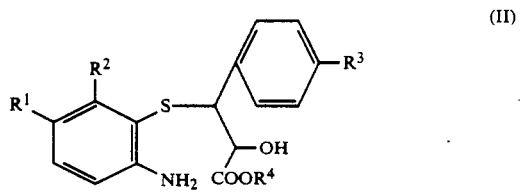

wherein $R^1$, $R^2$ and $R^3$ have the same meanings as defined above, and $R^4$ represents hydrogen atom or an ester residue, to intramolecular ring closing reaction in the presence of a sulfonic acid compound represented by the formula (III):

$R^5SO_3H$                   (III)

wherein $R^5$ represents a lower alkyl group or a substituted or unsubstituted phenyl group.

7 Claims, No Drawings

PROCESS FOR PREPARING 1,5-BENZOTHIAZEPINE DERIVATIVES

This is a continuation-in-part of co-pending parent application Ser. No. 07/507,929 filed Apr. 12, 1990, now abandoned.

BACKGROUND OF THE INVENTION

This invention relates to a novel process for preparing 1,5-benzothiazepine derivatives represented by the formula:

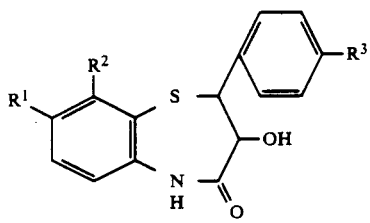
(I)

wherein one of $R^1$ and $R^2$ is a lower alkyl group or halogen atom, and the other is hydrogen, $R^3$ is a lower alkyl group or a lower alkoxy group.

The above 1,5-benzothiazepine derivatives (I) are useful as an intermediate for the synthesis of, for example, the corresponding 3-acetoxy-5-[2-(dimethylamino)ethyl]-1,5-benzothiazepine derivatives having excellent hypotensive activity.

Heretofore, as a process for preparing 1,5-benzothiazepine derivatives (I), the method in which a propionic acid derivatives represented by the formula:

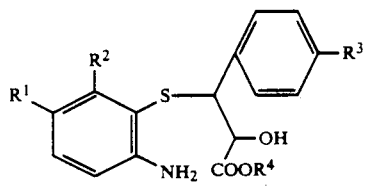
(II)

wherein $R^4$ represents hydrogen atom or an ester residue, and $R^1$, $R^2$ and $R^3$ have the same meanings as defined above, is heated in a solvent (for example, xylene) to effect intramolecular ring closing has been known (U.S. Pat. Nos. 4,567,175 and No. 4,590,188). However, this method involves the problem of requiring a long period of time for the intramolecular ring closing reaction.

SUMMARY OF THE INVENTION

The present inventors have studied various research and as a result, they have found that, when the intramolecular ring closing reaction of the compound (II) is carried out in the presence of a specific sulfonic acid compound, the compound (I) can be prepared by the reaction within a short time with good yield. The present invention has been established based on such findings.

That is, according to the process of the present invention, the 1,5-benzothiazepine derivatives represented by the formula (I) can be prepared by subjecting a propionic acid derivative represented by the formula (II):

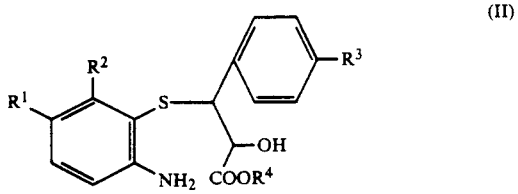
(II)

wherein $R^1$, $R^2$, $R^3$ and $R^4$ have the same meanings as defined above, to intramolecular ring closing reaction in the presence of a sulfonic acid compound represented by the formula (III):

$$R^5SO_3H \qquad (III)$$

wherein $R^5$ represents a lower alkyl group or a substituted or unsubstituted phenyl group.

DESCRIPTION OF THE PREFERRED EMBODIMENTS

Examples of the sulfonic acid compound (III) to be used in the intramolecular ring closing reaction of the present invention include, for example, the compounds wherein $R^5$ in the formula (III) is an alkyl group having 1 to 4 carbon atoms such as methyl group, ethyl group, propyl group or butyl group or a phenyl group which may be substituted by at least one of these alkyl groups, and particularly, methanesulfonic acid or p-toluenesulfonic acid is preferably used. An amount of the said sulfonic acid is not particularly limited but generally it is preferably used at an amount of 0.5 to 10 w/w %, more preferably about 1 to about 6 w/w % based on the compound (II).

The present intramolecular ring closing reaction is preferably practiced in an appropriate solvent under reflux. As the solvent, high boiling point solvents such as xylene, toluene and dichlorobenzene are preferably used, and xylene is particularly preferably used. A reaction time may be extremely short as compared with the case where no sulfonic acid compound is present in the reaction system, and for example, when xylene is used as a solvent, the reaction can be terminated at about 30 minutes to about 4 hours.

The desired compound (I) formed can be isolated as a pure product containing no sulfonic acid compound (III) by simple and easy operations as, for example, cooling the reaction mixture, collecting precipitated crystals by filtration, and washing with a suitable solvent (e.g. ethanol, aqueous ethanol, etc.).

The thus obtained compound (I) can be converted to the corresponding 3-acetoxy-5-($\beta$-dimethylaminoethyl)-1,5-benzothiazepine derivatives represented by the formula:

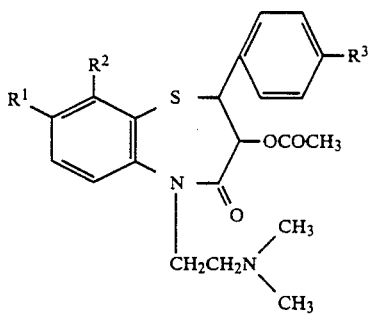

(VI)

wherein $R^1$, $R^2$ and $R^3$ have the same meanings as defined above, or a pharmaceutically acceptable salt thereof in a known method, for example, in a method described in U.S. Pat. Nos. 4,567,175 and No. 4,590,188, the contents of which are hereby incorporated herein by reference.

According to the process of the present invention as mentioned above, the intramolecular ring closing reaction can be terminated within a short period of time and the desired compound can be obtained in high yield and high purity. Therefore, the process of the present invention is extremely excellent from the industrial viewpoint as compared with the conventional process in which the reaction is performed in the absence of the sulfonic acid compound.

The starting compound (II) can be prepared according to the method as disclosed in Japanese Provisional Patent Publication No. 225174/1984 or No. 202871/1985, but an optically active compound (II) wherein $R^4$ is an ester residue, i.e. an optically active threo-propionic acid ester derivative represented by the formula:

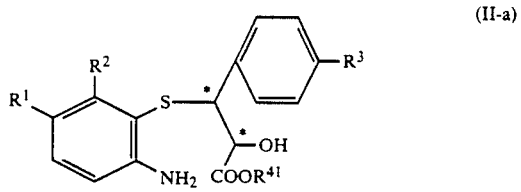

(II-a)

wherein $R^{41}$ represents an ester residue, * represents said carbon tom is an asymmetric carbon atom, and $R^1$, $R^2$ and $R^3$ have the same meanings as defined above, can be prepared by reacting a thiophenol compound represented by the formula:

(IV)

wherein symbols have the same meanings as defined above, with an optically active trans-glycidic acid ester represented by the formula:

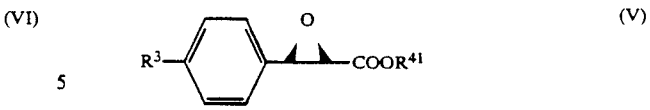

(V)

wherein symbols have the same meanings as defined above. The above reaction is preferably practiced in an appropriate solvent (e.g. xylene, toluene, etc.) under heating. The compound (II - a) may be isolated, but without isolation, the reaction mixture can be applied to the subsequent intramolecular ring closure reaction. In this case, the optically active desired compound (I) can be obtained from the compound (IV) in the same reaction vessel within a short period of time in good yield. Therefore, the process is industrially extremely advantageous.

Throughout the specification and claims, the term "lower alkyl" and "lower alkoxy" should be interpreted as referring to alkyl having one to four carbon atoms and alkoxy having one to four carbon atoms, respectively.

EXAMPLE 1

(1) In 400 ml of toluene are dissolved 24.0 g of 2-amino-5-chlorothiophenol and 31.2 g of (-)-trans-3-(4-methoxyphenyl)glycidic acid methyl ester and the solution is refluxed under nitrogen atmosphere for 2 hours. Diisopropyl ether is added to the reaction mixture, and precipitated crystals are collected by filtration to give 37.6 g of (+)-threo-2-hydroxy-3-(2-amino-5-chlorophenylthio)-3-(4-methoxyphenyl)propionic acid methyl ester as colorless needles.

Yield: 68%.

m.p. 126° to 129.5° C.

$[\alpha]_D^{20} +248.8°$ (c=0.3, methanol).

(2) A mixture of 9.5 g of the present product, 0.49 g of p-toluenesulfonic acid monohydrate and 95 ml of xylene is refluxed for 2 hours. After cooling, precipitated crystals are collected by filtration to give 7.5 g of (+)-cis-2-(4-methoxyphenyl) -3-hydroxy-8-chloro-2,3-dihydro-1,5-benzothiazepin-4(5H)-one.

Yield: 86.8%.

m.p. 244° to 245° C.

$[\alpha]_D^{20} +91.6°$ (c=1.0, dimethylformamide).

EXAMPLE 2

A mixture of 17.0 g of (+)-threo-2-hydroxy-3-(2-amino-5-chlorophenylthio) -3-(4-methoxyphenyl)propionic acid, 0.91 g of p-toluenesulfonic acid monohydrate and 220 ml of xylene is refluxed for 2 hours under continuous removal of water. After cooling, precipitated crystals are collected by filtration and washed with ethanol to give 15 g of (+)-cis-2-(4-methoxyphenyl)-3-hydroxy-8-chloro-2,3-dihydro-1,5-benzothiazepin-4(5H)-one.

Yield: 93%.

m.p. 244° to 245° C.

Incidentally, according to the method in which the above reaction is practiced in the absence of p-toluenesulfonic acid in the same manner as described in Japanese Provisional Patent Publication No. 225174/1984, yield of the desired compound is 73% even after refluxing for 20 hours.

EXAMPLE 3

A mixture of 17.0 g of (+)-threo-2-hydroxy-3-(2-amino-5-chlorophenylthio) -3-(4-methoxyphenyl)propionic acid, 0.91 g of p-toluenesulfonic acid monohydrate and 220 ml of toluene is refluxed for 8 hours under continuous removal of water. After cooling, precipitated crystals are collected by filtration and washed with ethanol to give 14.8 g of (+)-cis-2-(4-methoxyphenyl)-3-hydroxy-8-chloro-2,3-dihydro-1,5-benzothiazepin -4(5H)-one.

Yield: 92%.
m.p. 244° to 245° C.

EXAMPLE 4

(1) In 600 ml of xylene are dissolved 132 g of 2-amino-5-methylthiophenol and 200 g of (±)-trans-3-(4-methylphenyl)glycidic acid methyl ester and the solution is refluxed at 120° to 130° C. under nitrogen atmosphere for 4 hours. After cooling to 40° C., n-hexane is added to the reaction mixture, and the reaction mixture is stirred and then cooled to 10° C. Precipitated crystals are collected by filtration to give 218 g of (±)-threo-2-hydroxy-3-(2-amino-5-methylthiophenol) -3-(4-methylphenyl)propionic acid methyl ester as colorless crystals.

Yield: 69%.
m.p. 114° to 116° C.

(2) In 500 g of xylene are dissolved 50 g of the product, 0.57 g of p-toluenesulfonic acid monohydrate is added to the solution and the solution is refluxed for 4 hours. After cooling, precipitated crystals are collected by filtration, washed with xylene to give 39.0 g of (±)-cis-2-(4-methylphenyl) -3-hydroxy-8-methyl-2,3-dihydro-1,5-benzothiazepin-4(5H)-one as colorless crystals.

Yield: 86%.
m.p. 185° to 186° C.

EXAMPLE 5

In a solution of 200 ml of water and 100 g of methanol are suspended 40 g of (±)-threo-2-hydroxy-3-(2-amino-5-methylphenylthio)-3-(4-methylphenyl)propionic acid methyl ester, 7.4 g of potassium hydroxide are added to the suspension and the mixture is stirred for 30 minutes at 50° to 55° C. Then, 13.8 g of 35% hydrochloric acid are added dropwise, and 200 ml of water are added thereto, and the mixture is cooled to 10° C. Precipitated crystals are collected by filtration and washed with water to give 80 g of (±)-threo-2-hydroxy -3-(2-amino-5-methylphenylthio)-3-(4-methylphenyl)propionic acid (wet material).

This product (80 g) is suspended in 400 ml of toluene, and 0.4 g of p-toluenesulfonic acid monohydrate is added thereto and the mixture is refluxed for 5 hours under continuous removal of water. After cooling, precipitated crystals are collected by filtration, washed with toluene and dried to give 32.5 g of (±)-cis-2-(4-methylphenyl)-3-hydroxy-8-methyl-2,3-dihydro-1,5-benzothiazepin -4(5H)-one.

Yield: 90%.
m.p. 185° to 186° C.

EXAMPLE 66

In 400 ml of toluene are dissolved 24.0 g of 2-amino-5-chlorothiophenol and 31.2 g of (-)-trans-3-(4-methoxyphenyl)glycidic acid methyl ester, and the solution is refluxed under nitrogen atmosphere for 2 hours. To the reaction mixture are added 1.43 g of p-toluenesulfonic acid hydrate and 350 ml of xylene and the mixture is refluxed for 2 hours and simultaneously 350 ml of the solvent is distillated. After cooling, precipitated crystals are collected by filtration to give 19.8 g of (+)-cis-2-(4-methoxyphenyl)-3-hydroxy-8-chloro-2,3-dihydro-1,5-benzothiazepin-4(5H)-one.

Physical and chemical properties of the product were identical to those of the product obtained in Example 1.

EXAMPLE 7

(1) In 420 ml of xylene are dissolved 42 g of 2-amino-5-methylthiophenol and 58 g of (+)-trans-3-(4-methylphenyl)-glycidic acid methyl ester, and the solution is refluxed under nitrogen atmosphere for 2 hours. After cooling, n-hexane is added to the reaction mixture and precipitated crystals are collected by filtration to give 65 g of (-)-threo-2-hydroxy-3-(2-amino-5-methylphenylthio)-3-(4-methylphenyl)-propionic acid methyl ester as colorless needles.

Yield: 65%.
m.p. 107° to 109° C.
$[\alpha]_D^{20}$- 235.4° (c=1, methanol).

(2) A mixture of 20 g of the above product, 0.4 g of p-toluenesulfonic acid monohydrate and 160 ml of xylene is refluxed for 5 hours. After cooling, precipitated crystals are collected by filtration to give 15.7 g of (-)-cis-2-(4-methylphenyl)-3-hydroxy-8-methyl-2,3-dihydro-1,5-benzothiazepin-4(5H)-one.

Yield: 87%.
m.p. 207° to 212° C.
$[\alpha]_D^{20}$ - 120° (c=0.3, methanol).

We claim:

1. A process for preparing optically active cis-1,5-benzothiazephine derivatives represented by the formula:

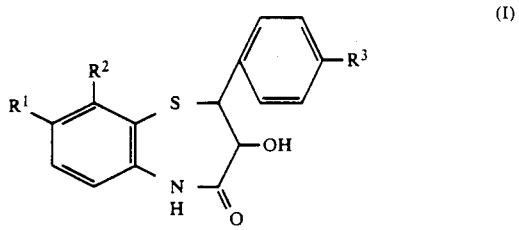

(I)

wherein one of $R^1$ and $R^2$ is a lower alkyl group or halogen atom, and the other is hydrogen atom, $R^3$ is a lower alkyl group or a lower alkoxy group, and * represents said carbon atom is an asymmetric carbon atom, which comprises reacting a thiophenol compound represented by the formula (IV):

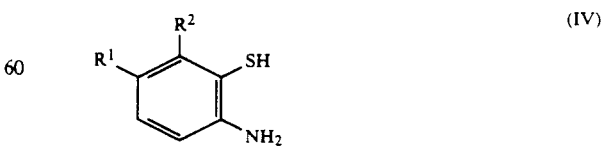

(IV)

wherein $R^1$ and $R^2$ have the seam meanings as defined above,
with an optically active trans-glycidic acid ester represented by the formula:

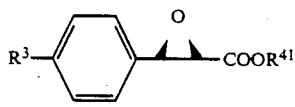

wherein $R^3$ has the same meaning as defined above, and $R^{41}$ represents an ester residue, to form an optically active threo-propionic acid ester compound represented by the formula:

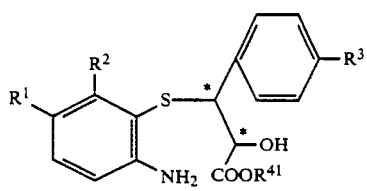

wherein $R^1$, $R^2$, $R^3$, $R^{41}$ and * have the same meanings as defined above,
and then subjecting the above compound (II - a) to intramolecular ring closing reaction in the presence of a sulfonic acid compound represented by the formula (III):

$$R^5SO_3H \qquad (III)$$

wherein $R^5$ represents a lower alkyl group or a substituted or unsubstituted phenyl group.

2. A process for preparing 1,5-benzothiazepine derivatives according to claim 1, wherein the reaction of the thiophenol compound (IV) and the optically active transglycidic acid ester (V) is carried out in an appropriate solvent under heating.

3. A process for preparing 1,5-benzothiazepine derivatives according to claim 1, wherein $R^5$ in the the sulfonic acid compound (III) is methyl group, ethyl group, propyl group, butyl group or phenyl group which may be substituted by at least one selected from methyl group, ethyl group, propyl group and butyl group.

4. A process for preparing 1,5-benzothiazepine derivatives according to claim 3, wherein the sulfonic acid compound (III) is methanesulfonic acid or p-toluenesulfonic acid.

5. A process for preparing 1,5-benzothiazepine derivatives according to claim 1, wherein the intramolecular ring closing reaction is carried out in an appropriate solvent under reflux.

6. A process for preparing 1,5-benzothiazepine derivatives according to claim 1, wherein the sulfonic acid (III) is used at an amount of 0.5 to 10 w/w % based on the compound (II - a).

7. A process for preparing 1,5-benzothiazepine derivatives according to claim 6, wherein the sulfonic acid (III) is used at an amount of 1 to 6 w/w % based on the propionic acid compound (II - a).

* * * * *